(12) United States Patent
Lopez et al.

(10) Patent No.: US 10,016,586 B2
(45) Date of Patent: Jul. 10, 2018

(54) CONNECTOR FOR MEDICAL USE

(71) Applicant: CAIR L.G.L., Lissieur (FR)

(72) Inventors: Georges Antoine Lopez, Ecully (FR); Patrick Delorme, Chaponost (FR)

(73) Assignee: CAIR L.G.L., Lissieu (FR)

( * ) Notice: Subject to any disclaimer, the term of this patent is extended or adjusted under 35 U.S.C. 154(b) by 33 days.

(21) Appl. No.: 14/407,374

(22) PCT Filed: Aug. 8, 2013

(86) PCT No.: PCT/FR2013/051912
§ 371 (c)(1),
(2) Date: Dec. 11, 2014

(87) PCT Pub. No.: WO2014/023921
PCT Pub. Date: Feb. 13, 2014

(65) Prior Publication Data
US 2015/0126942 A1 May 7, 2015

(30) Foreign Application Priority Data
Aug. 10, 2012 (FR) ...................................... 12 57767

(51) Int. Cl.
*A61M 39/10* (2006.01)
*A61M 39/26* (2006.01)

(52) U.S. Cl.
CPC ............ *A61M 39/10* (2013.01); *A61M 39/26* (2013.01); *A61M 2039/1066* (2013.01); *A61M 2039/1077* (2013.01); *A61M 2039/267* (2013.01)

(58) Field of Classification Search
CPC ................. A61M 39/10; A61M 39/26; A61M 2039/1072; A61M 2039/268;
(Continued)

(56) References Cited

U.S. PATENT DOCUMENTS 5,549,566 A * 8/1996 Elias ................... A61M 39/045
604/167.03
6,113,068 A * 9/2000 Ryan ................... A61M 39/045
251/149.4

(Continued)

FOREIGN PATENT DOCUMENTS

EP 1890760 B1 6/2008
WO WO-96/13301 A2 5/1996
(Continued)

OTHER PUBLICATIONS

International Search Report issued in PCT/FR2013/051912 mailed on Oct. 02, 2013.

*Primary Examiner* — Nathan R Price
*Assistant Examiner* — Weng Lee
(74) *Attorney, Agent, or Firm* — Marshall, Gerstein & Borun LLP

(57) ABSTRACT

A connector for a medical use comprising a fitting secured to a chamber, the fitting being provided at its center with a needle encased at least in its terminal portion in the recess of an elastic seal having, across the thickness of its free end, a slit or the like, the elastic seal being further provided with a ring. A terminal end of the elastic seal has a deformable peripheral rim overlapping the end of said ring.

12 Claims, 7 Drawing Sheets

(58) Field of Classification Search
CPC .... A61M 2039/267; A61M 2039/2077; A61M 2039/1066
See application file for complete search history.

(56) References Cited

U.S. PATENT DOCUMENTS

2005/0151105 A1* 7/2005 Ryan ............... A61M 39/26
                                              251/149.6
2008/0249508 A1* 10/2008 Lopez ............. A61M 39/10
                                              604/533
2011/0282302 A1* 11/2011 Lopez ............. A61M 39/10
                                              604/247

FOREIGN PATENT DOCUMENTS

WO  WO-97/21464 A1  6/1997
WO  WO-2011/064738 A2  6/2011

* cited by examiner

FIG. 9
FIG. 10
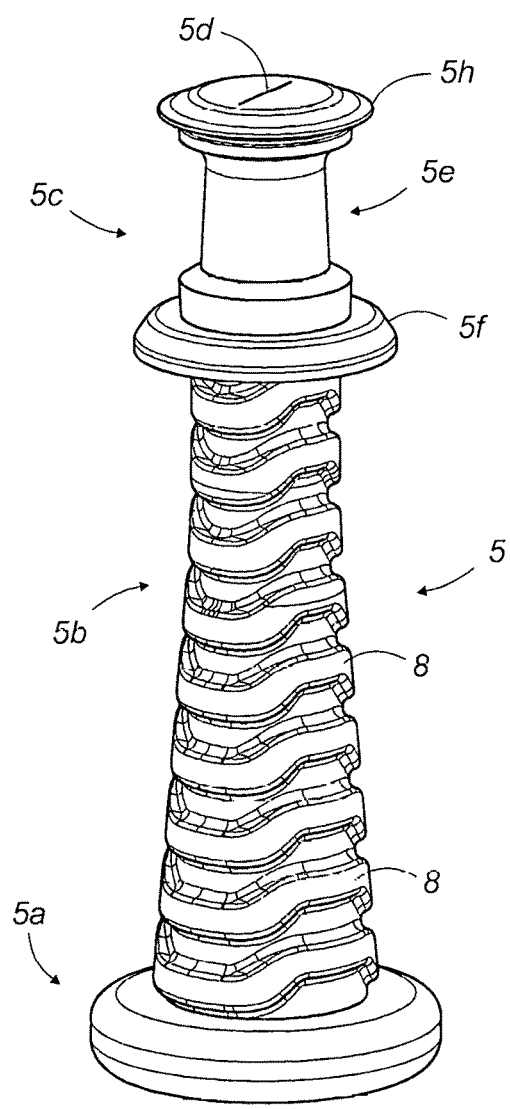
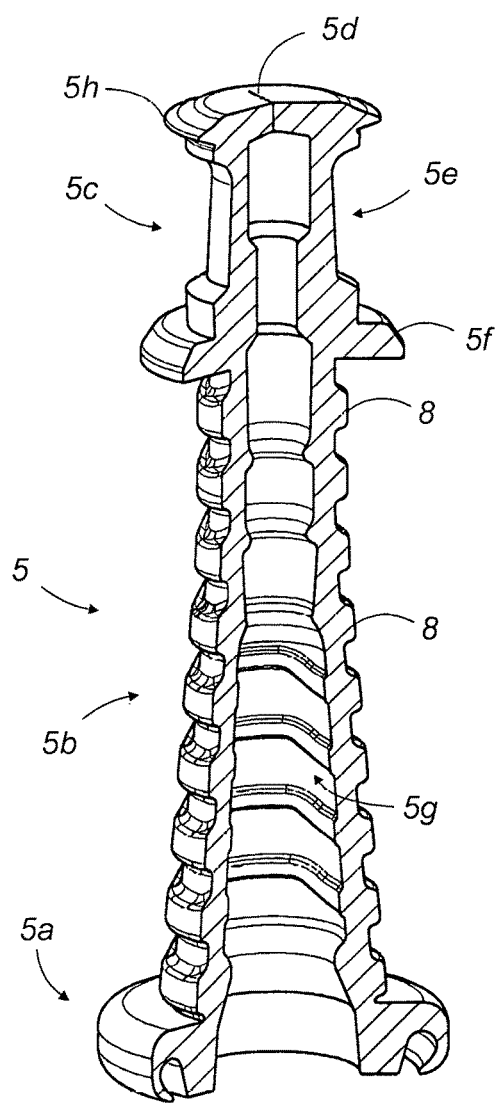

CONNECTOR FOR MEDICAL USE

CROSS REFERENCE TO RELATED APPLICATIONS

This application is a national phase application of PCT/FR2013/051912, filed Aug. 8, 2013, and published as WO 2014/023921 A1, and claims the benefit of priority of French application 1257767, filed Aug. 10, 2012, which is hereby incorporated by reference herein in its entirety for all purposes.

TECHNICAL FIELD

The present invention relates to the technical field of connectors for medical use, and more specifically relates to a connector for medical use for the distribution of a fluid, of the type comprising a chamber secured to a fitting provided with a needle, an elastic seal, and a ring.

BACKGROUND

A connector for medical use having a first end also referred to as "upstream end" intended to be connected to a pipe conducting a fluid; and a second end also referred to as "downstream end" intended to cooperate with a device for sampling or injecting said fluid via a connector of male Luer type is known from document EP 1890760. In the following, expressions "upstream end" and "downstream end" will be used regardless of the fluid flow direction.

In practice, the connector has a chamber secured at its base to a fitting forming the upstream end of the actual connector. The free end of the chamber, opposite to the base, is intended to receive, by friction, the tip of a male Luer connector. The flowing of the fluid between the pipe connected to the upstream end of the connector and the end of the male Luer is ensured by means of a needle secured to the body of the fitting. The needle extends in the chamber and emerges into the terminal end of said chamber.

The needle is encased and maintained within the recess of an elastic seal having, across the thickness of its free terminal end, a slit or the like enabling the needle to pass when the elastic seal is compressed in the connected position of the connector.

The elastic seal has a free end tangent to the free end of the chamber and is provided with a ring encircling its terminal portion all the way to the area opposite the lateral hole(s) of the needle.

Further, along a portion of the length of the terminal end of the chamber, the external surface of the elastic seal and/or the internal surface or the thickness of the ring has at least one recess intended to ensure the retreat of the material forming the seal, at the passing of the needle.

In practice, the internal cross-section of the terminal compartment of the chamber may be cylindrical or of female Luer type, that is, with a 6% Luer cone. To ensure the guiding of the elastic seal, the ring portion contained in the central compartment of the chamber has a cylindrical shape.

To ensure the system tightness, that is, the tightening of the elastic seal causing the closing of the slit, the external cross-section of the seal in contact with the ring downstream of the recess of said ring is greater than the corresponding internal cross-section of the ring. However, upstream of the recess(es), the external cross-section of the seal is substantially equal to the internal cross-section of the ring.

Further, the guiding of the seal in the chamber is ensured by the ring only, having all or part of its wall in sliding contact with the corresponding wall of the chamber for the entire duration of the elastic seal motion, from its relaxed position to its compressed position. Due to the plastic nature of the materials used, there is only a minimum friction force between the chamber and the ring.

However, although it is quite satisfactory, the connector which has just been described can further be improved.

First, since the ring has a cylindrical shape and the end of the chamber has a Luer shape, there necessarily remains a space between the ring and the internal wall of the free end of the chamber (see FIG. 2). Small though this space may be, contamination risks remain possible.

Further, since the contact surface area between the Luer cone of the sampling device or the like and the connector is formed by the free end of the ring only, the tightness between the two elements is not optimal, the two surfaces being made of rigid plastic material.

Finally, the discontinuous configuration of the free end of the connector, which alternates, from the center to the periphery, independent materials of different nature (the resilient portion, the ring, a space, and finally the chamber wall) does not enable either to properly decontaminate the end of the connector after disconnection.

Document WO96/13331 described a connector for medical use comprising a fitting secured to a chamber and provided at its center with a needle comprising at least one lateral hole. The needle is encased, at least in its terminal portion, in the recess of an elastic seal. The elastic seal has a slit across the thickness of its free end, and is provided with a ring encircling its terminal portion, upstream of the needle hole, in disconnected position of the connector. The peripheral rim of the elastic seal enables to ensure a sliding motion and a proper alignment of the elastic seal on insertion of the sampling device or the like in the cylindrical portion of the connector. It should particularly be specified that this peripheral rim does not change the tightness properties of said connector.

SUMMARY

The invention aims at overcoming the above-mentioned disadvantages by providing a connector for a medical use which allows a connection of optimal tightness.

Another object of the invention is to provide a connector which is as little subject to bacterial contamination as possible.

To achieve these objects, a connector for a medical use comprising a fitting secured to a chamber has been developed. The fitting is provided at its center with a needle extending in said chamber and emerging into its terminal end. The terminal end of said chamber has a cross-section capable of receiving, by friction, a connector of male Luer type. The needle is provided with at least one through lateral hole and is arranged at least in its terminal portion, including the hole(s), in the recess of an elastic seal having, across the thickness of its free end, a slit or the like. The elastic seal is further provided with a ring encircling its terminal portion at least all the way to the area opposite the needle hole(s), and this, when the connector is not connected.

According to the invention, the terminal end of the elastic seal has a deformable peripheral rim covering the free end of said ring.

Due to the overlapping of the deformable peripheral rim on the free end of said ring, the space present between said ring and the internal wall of the chamber at the level of its terminal end is limited. This results in limiting the risk of bacterial contamination at this level.

To further limit the contamination in the space formed between the ring and the chamber wall, the deformable peripheral rim is advantageously in contact with the internal wall of the chamber along its entire circumference.

In parallel, since the contact between the male Luer cone of the sampling device or the like and the ring is no longer direct, but performed via a resilient material, the tightness in connected position is reinforced.

To leave no space or nook capable of forming contamination sources between the terminal end of the elastic seal and the free end of the chamber, the deformable peripheral rim is in contact with the internal edge of the free end of the chamber and is advantageously positioned flush therewith.

Preferably, in the medical connector according to the invention, the deformable peripheral rim of the terminal end of the elastic seal is tangent to the free end of the chamber. In other words, the deformable peripheral rim and the surface of the free end of the chamber are in a same plane. Thereby, the terminal surface of the connector is planar and a surface continuity is provided between the free end of the chamber and the elastic seal.

In a specific embodiment of the medical connector according to the invention, the deformable peripheral rim of the terminal end of the elastic seal has the shape of a V, with its tip directed towards the internal wall of the chamber.

Thus, in connected position, the peripheral rim of the seal is sandwiched between the Luer cone of the sampling device or the like and the downstream end of the ring.

The tightness is thus optimal. In practice, the peripheral rim of the seal curves upwards when the elastic seal passes to a compressed position and is submitted to a symmetrical deformation, that is, curves downwards, when the elastic seal returns to its relaxed position.

Further, the V shape of the deformable peripheral rim enables to optimally adjust the flush position of said rim with respect to the internal edge of the free end of the chamber and to obtain a continuity of said free end of the chamber with the elastic seal. Contamination risks are suppressed.

Further, the free surface of the connector is continuous, which facilitates the connector decontamination after use.

According to a specific embodiment, in the connector according to the invention, the elastic seal has a substantially conical shape and comprises a base-forming portion, a median portion, and a terminal portion covered with the ring.

Advantageously, the wall of said median portion comprises a succession of beads defining, along the circumference of said seal, a wavy shape symmetrical with respect to an axial plane of said elastic seal.

According to a specific embodiment, the wavy shape corresponds to two sinusoid periods.

In a preferred embodiment, the wall of said median portion comprises, along the circumference of said seal, a succession of non-through cavities having elliptic shapes, offset by one half-step every 90° around said circumference.

These different embodiments of the median wall of the elastic seal enable to improve the flexibility of said seal and also to facilitate the disengagement of the needle. This also enables to improve the resilient properties of the seal so that it can take a compressed position when the connector is connected, and automatically return to a relaxed position when the connector is disconnected.

Further, and according to another characteristic, the base of the seal has a continuous peripheral groove directed upstream of the connector enabling to avoid for the liquid volume likely to flow into the space separating the needle from the internal wall of the seal to leak into the chamber.

Indeed, under the effect of the pressure exerted during the seal compression, the liquid lodges into the groove and thus exerts a pressure of the base of the elastic against the chamber wall. Any risk of back leakage is thus avoided.

BRIEF DESCRIPTION OF THE DRAWINGS

The foregoing and other features and advantages of the present invention will be discussed in detail in the following non-limiting description, in connection with the accompanying drawings, among which:

FIG. 9 is a simplified perspective view of a specific embodiment of the elastic seal present in the connector for medical use according to the invention;

FIG. 10 is a simplified view similar to that of FIG. 9, the elastic seal being truncated along a plane crossing the longitudinal axis of said seal;

DETAILED DESCRIPTION

Figure 1:
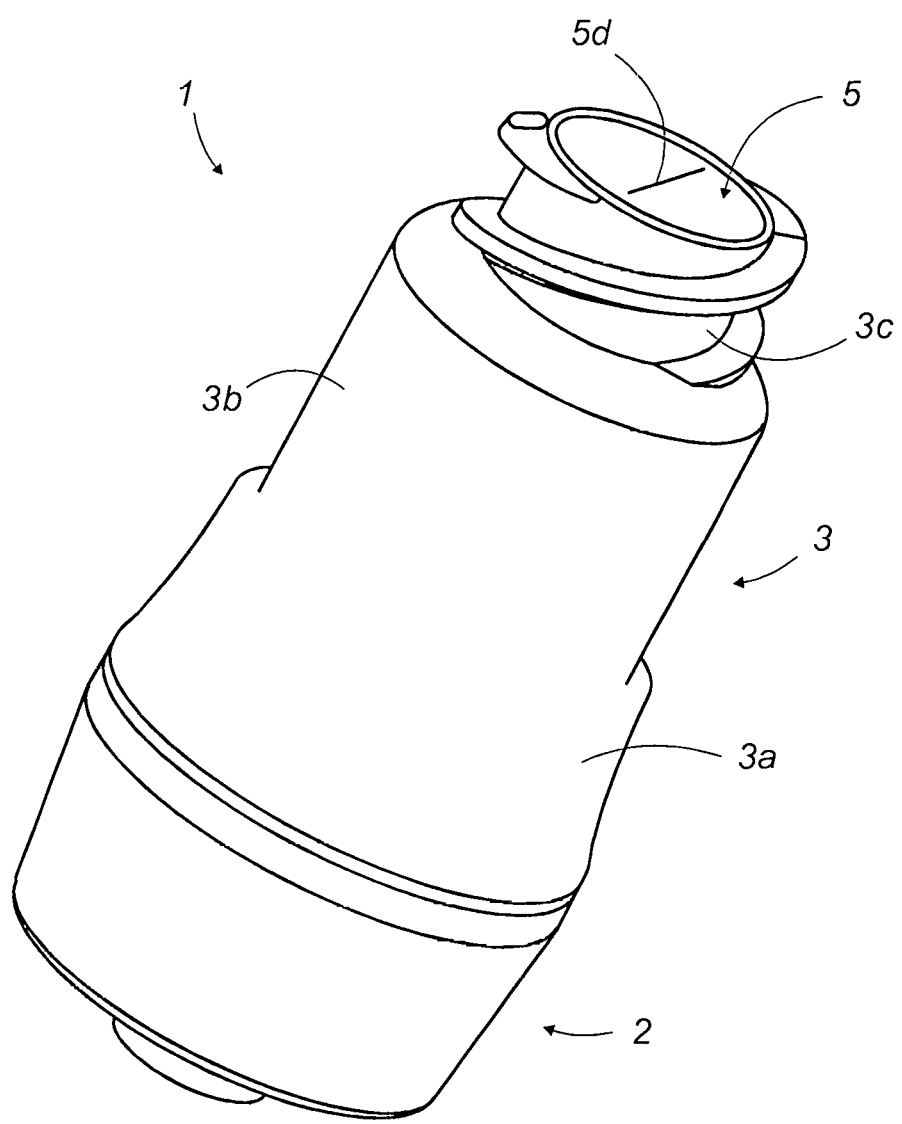
FIG. 1 is a simplified perspective view of a connector for medical use according to the invention.

Referring to FIG. 1 which shows a medical connector (1) according to the invention, the latter comprises a fitting (2) secured to a chamber (3) as well as a ring (4) (not shown in this drawing)/elastic seal (5) assembly. The fitting (2) appears in the form of a composite part associating the body of the actual fitting (2) and a needle (6) (not shown in this drawing). The chamber (3) comprises a first compartment (3a), a central compartment (3b), and a terminal compartment (3c).

Figure 2:
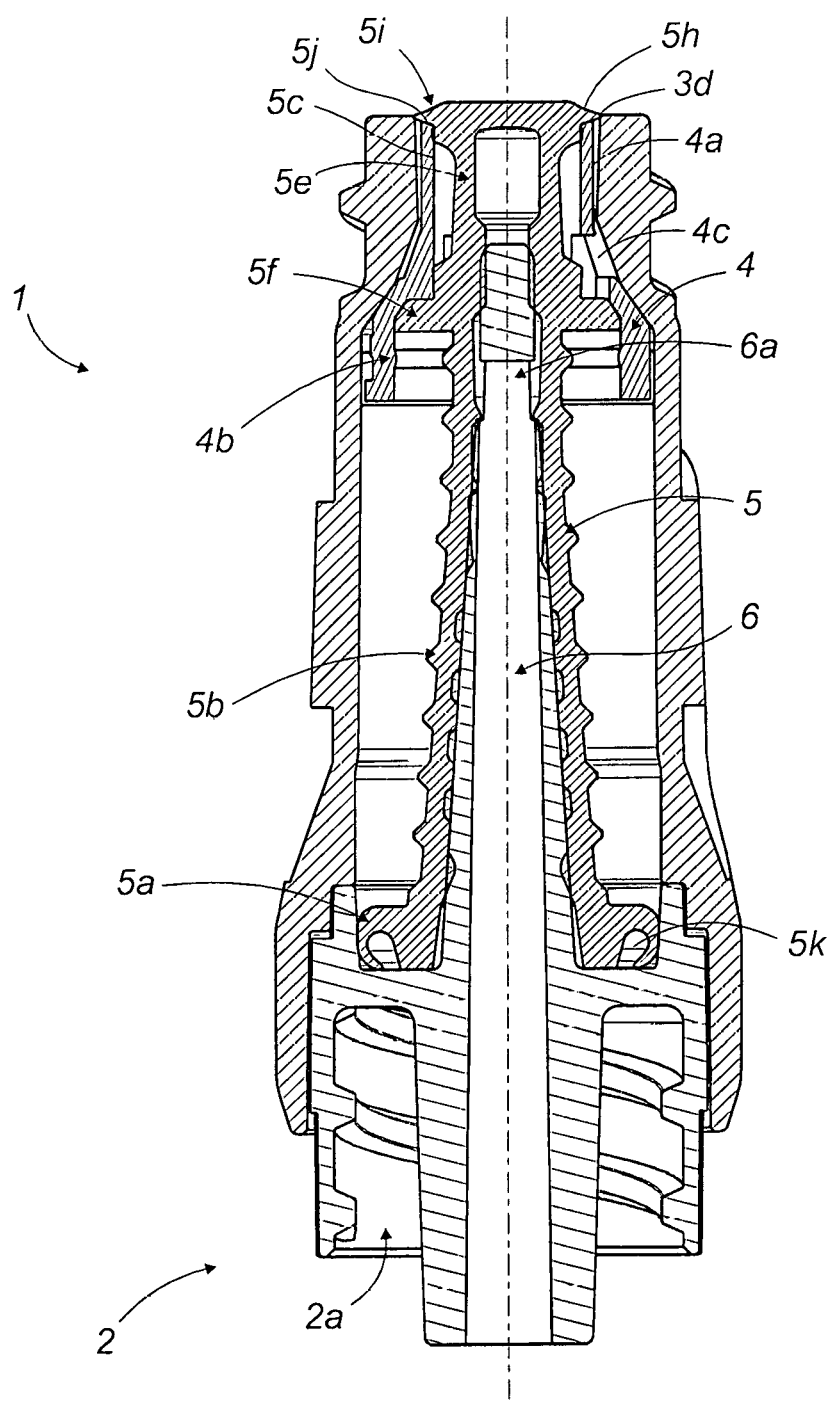
FIG. 2 is a simplified longitudinal cross-section view of the connector for medical use according to the invention.
Figure 3:
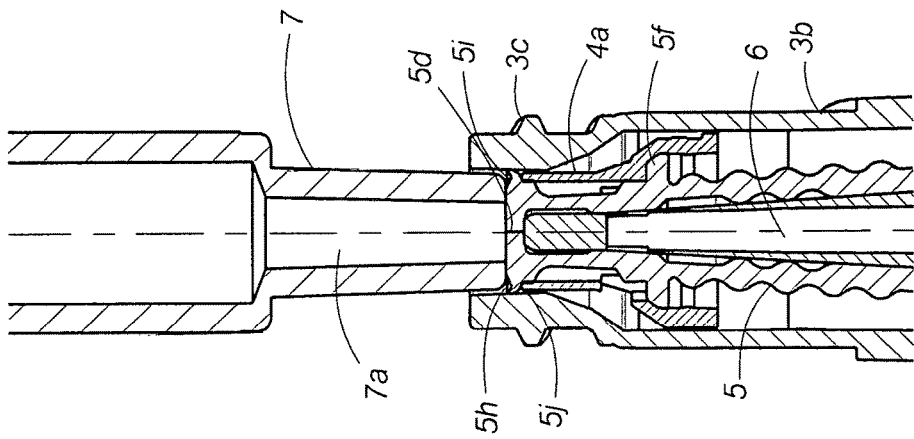
FIGS. 3 to 8 are simplified views showing in detail the terminal end of the connector for medical use, as well as the deformation of the elastic seal, at different successive steps of connection and disconnection of the connector according to the invention.
Figure 4:
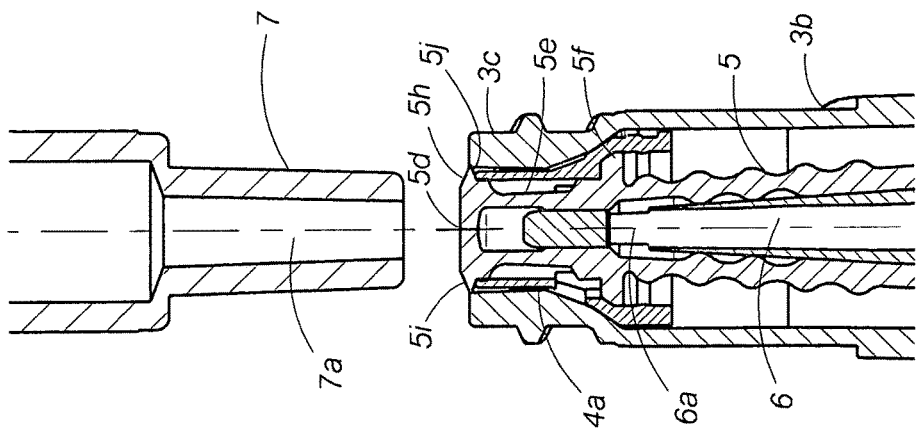
Figure 5:
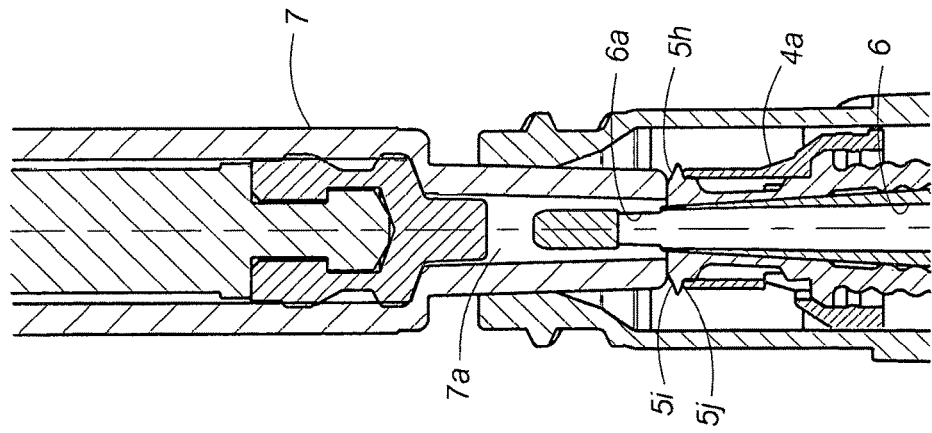

The terminal compartment (3c) of the chamber (3) has a cross-section capable of receiving, by friction, a connector (7) of male Luer type. The first compartment (3a) of the chamber (3) cooperates with the fitting (2), intended to receive a pipe conducting a fluid. Referring to FIG. 2 which shows the medical connector (1) according to the invention, in longitudinal cross-section, the body of the fitting (2) comprises a recess (2a), provided on its internal surface with a screw thread intended to cooperate with a corresponding screw thread of a pipe or of another female Luer connector capable of conducting a fluid. The body of the fitting (2) is provided at its center with a needle (6) extending from the first compartment (3a) towards the terminal end of the central compartment (3b).

The actual needle (6) is provided, close to its free end, itself closed, with two lateral holes (6a) having the fluid flowing therethrough. The needle (6) is placed in the cavity of an elastic seal (5) provided with a ring (4) encircling its terminal portion at least all the way to the area opposite the holes (6a) of the needle (6). This needle (6) has a substantially conical shape to facilitate its disengagement under the effect of the pushing force exerted by the connector (7) of male Luer type on the ring (4)/elastic seal (5) assembly.

Referring to FIGS. 9 to 12, elastic seal (5) is made of silicone and appears in the form of a tube having a conical external cross-section, intended to extend in the chamber (3)

from the body of the fitting (2) all the way to the free end of the terminal compartment (3c) of the chamber (3). The seal (5) comprises a base-forming portion (5a), a median portion (5b), and a terminal portion (5c).

The base-forming portion (5a) of the elastic seal (5) is intended to rest on the body of the fitting (2). In non-compressed position, that is, in relaxed position, neither the base-forming portion (5a) of the elastic seal (5), nor the median portion (5b) are in contact with the chamber (3). The base-forming portion (5a) is provided with a continuous groove (5k) intended to avoid back leakage problems, as previously explained.

The median portion (5b) of the elastic seal (5) has a substantially conical shape and comprises in a first embodiment, illustrated in FIGS. 9 and 10, a succession of beads (8) defining, along the circumference of said seal (5), a wavy shape symmetrical with respect to an axial plane of said elastic seal (5). This wavy shape corresponds to two sinusoid periods. In other words, the shapes of the beads (8) may be assimilated to toric shapes sunk on two opposite sides.

Figure 11:
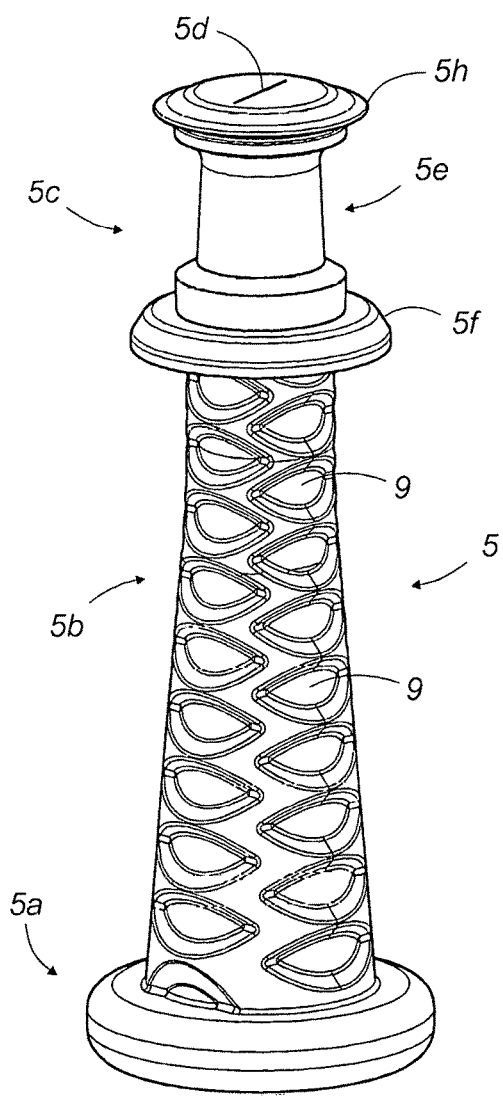
FIGS. 11 and 12 respectively are simplified views similar to those of FIGS. 9 and 10, showing another embodiment of the elastic seal.
Figure 12:
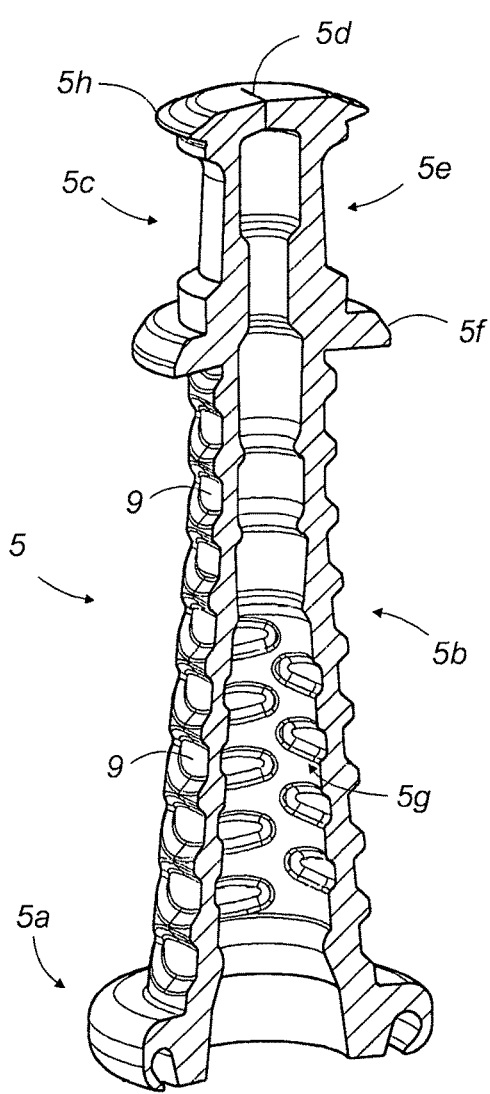

In a second embodiment, illustrated in FIGS. 11 and 12, the wall of said median portion (5b) of the elastic seal (5) comprises along the circumference of said seal (5), a succession of non-through cavities (9) of elliptic shapes offset by one half-step every 90° around said circumference. The circumference thus has a sort of cellular wall, having almond-shaped cells. Expression "offset by one half-step" means in the case in point offset by one half-cavity (9).

These different embodiments of the median wall (5b) of the elastic seal (5) enable to improve the flexibility of said seal (5) and also to facilitate the disengagement of the needle (6). This also enables to improve the elastic properties of the seal (5) so that it can take a compressed position when the connector (1) is connected, and automatically return to a relaxed position when the connector (1) is disconnected.

The terminal portion (5c) of the elastic seal (5) is provided with a slit (5d), allowing the passage of the needle (6), when the elastic seal (5) is in a so-called "compressed" position, in other words, when the connector (1) is connected to a connector (7) of male Luer type. The terminal portion (5c) of the elastic seal (5) further comprises a recess (5e) downstream of the end of the needle (6) in non-compressed position of the elastic seal (5). The terminal portion (5c) also has a flange (5f), which enables to guide and to center said terminal portion (5c) of the elastic seal (5) in the central compartment (3b) of the chamber (3). To take into account the shape and the dimensions of the central compartment (3b) of the chamber (3), this flange (5f) is also encircled by the ring (4).

Referring to FIGS. 10 and 12, elastic seal (5) has at its center a recess (5g) having a shape corresponding to that of the needle (6), the recess (5g) being however slightly longer than the needle (6).

The internal cross-section of the elastic seal (5) is smaller than the cross-section of the needle (6), even in the terminal area of the needle (6) covered with the ring (4), and including the lateral holes (6a), at the level of which the internal cross-section of the elastic seal (5) is smaller than the cross-section of the needle (6).

The ring (4) is positioned at the end of elastic seal (5) and has two segments of different cross-sections, respectively, a first cylindrical segment (4a) encircling the terminal portion (5c) of the elastic seal (5) along a length corresponding to the length of the terminal compartment (3c) and having a cross-section substantially equal to the cross-section of said terminal compartment (3c) and a second cylindrical segment (4b), having an upper cross-section substantially equal to the corresponding cross-section of the central compartment (3b) and covering the flange (5f) of the elastic seal (5). The ring (4) is made of a rigid or semi-rigid material, possibly of bi-material with the elastic seal (5), or separately, the ring (4) and the seal (5) being secured to each other particularly by gluing or simple appending. The external cross-section of the seal (5) is substantially equal to the internal cross-section of the ring (4) on their overlapping area.

According to a feature of the invention, the terminal end of the elastic seal (5) has a deformable peripheral rim (5h) overlapping the end of said ring (4). This peripheral rim (5h) has an upper peripheral chamfer (5i) and a lower peripheral chamfer (5j). The two chamfers (5i, 5j) are manufactured to join in order to give a V shape to said peripheral rim (5h), with its tip oriented toward the internal wall of the chamber (3).

The V shape of the deformable peripheral rim (5h) enables to optimally adjust the flush position of said rim (5h) with respect to the internal edge (3d) of the free end of the chamber (3) and to obtain a continuity of said free end of the chamber (3) with the elastic seal (5). Risks of bacterial contamination are very significantly suppressed.

In "relaxed" position of the elastic seal (5), and to leave no space or nook capable of forming contamination sources remain between the terminal end of the elastic seal (5) and the free end of the chamber (3), the tip of the V of the deformable peripheral rim (5h) is in contact with the internal edge (3d) of the free end of the chamber (3) and is advantageously positioned flush therewith.

Referring to FIGS. 3 to 8, the internal wall of the terminal compartment (3c) of the chamber (3) having a Luer profile, that is, a 6% cone, the deformable peripheral rim (5h) is intended to deform when the seal takes a compressed position, or returns to a relaxed position. Thus, when the elastic seal (5) takes a compressed position, the deformation of the deformable peripheral rim (5h) against the internal Luer wall of the free end of the chamber (3) is facilitated. More specifically, said peripheral rim (5h) sandwiched between the cone (7a) of the connector (7) and the ring (4) curves upwards when the elastic seal (5) takes a compressed position, and undergoes a symmetrical deformation, that is, curves downwards when the elastic seal (5) recovers its relaxed position.

As shown in FIG. 2, the terminal portion, and more specifically the first cylindrical cross-section (4a) of the ring (4) has two openings (4c) intended to favor the retreat of the plastic material on passing of the needle (6) under the effect of the pushing force created by the installation of the connector (7) of male Luer type.

As illustrated in FIG. 2, the central compartment (3b) and the terminal compartment (3c) are connected by a shouldering used as a stop for the ring (4) encircling the terminal end (5c) of the elastic seal (5) in idle position, that is, in relaxed position of the seal, thus guaranteeing that the deformable peripheral rim (5h) of the elastic seal (5) is flush with the internal edge (3d) of the free end of the chamber (3).

Figure 6:
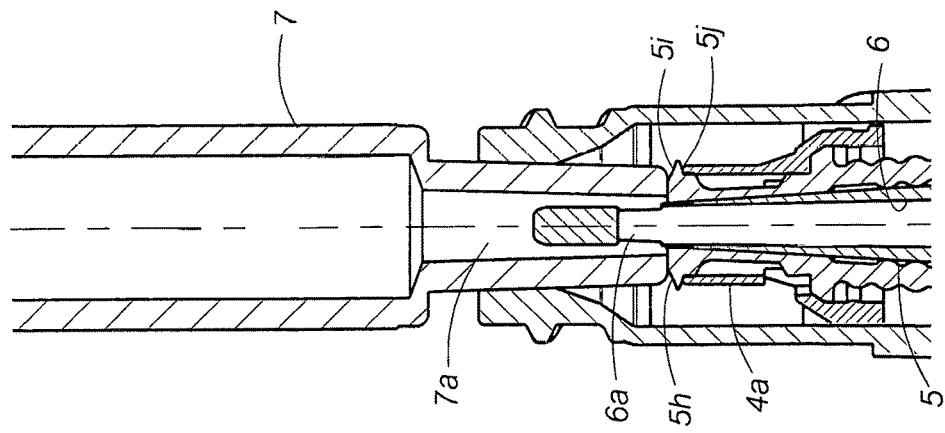
Figure 7:
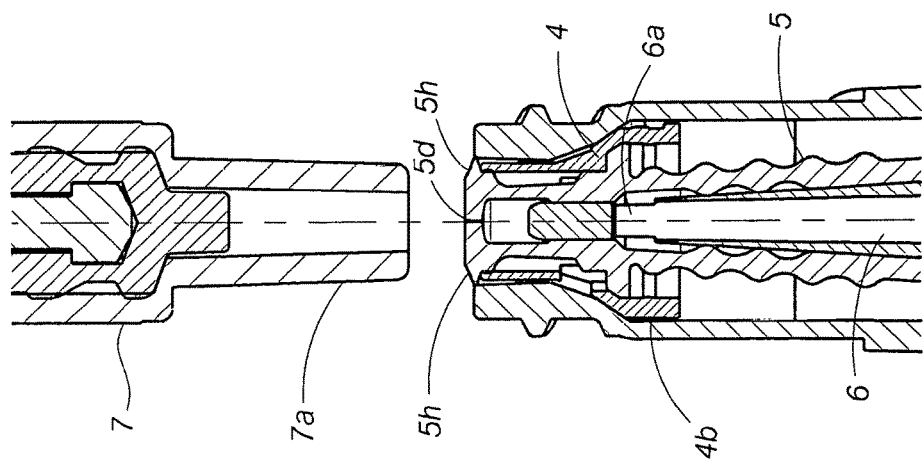
Figure 8:
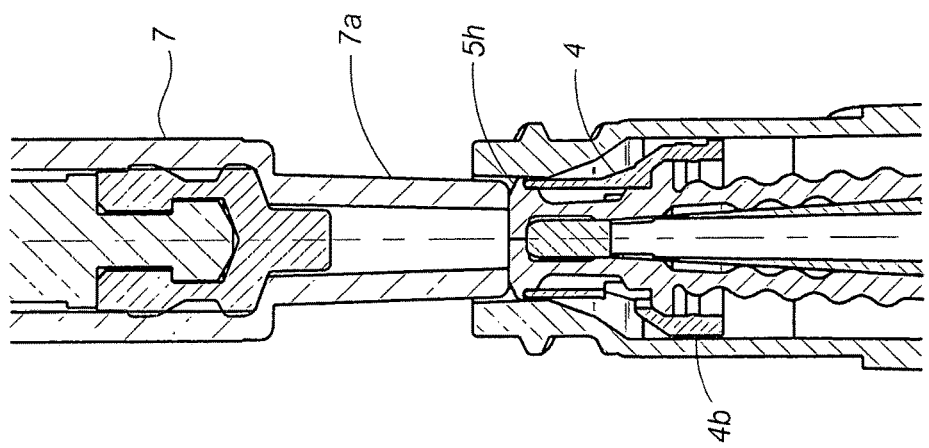

The connected position is more specifically shown in FIG. 6 by the installation of a connector (7) of male Luer type. This connector (7) is further provided with a Luer cone (7a), intended to be inserted into the aperture of the terminal compartment (3c) of the chamber (3). In practice, the cone (7a) pressed with its end on the free end of the elastic seal (5). This pressure causes the displacement of the elastic seal (5) along the shaft of the needle (6) towards the fitting (2), and then the passing of the point of the needle (6) through the slit (5d), facilitated by the recesses (5e), and finally the clearing of the lateral holes (6a), thus allowing the fluid to flow. The presence of the peripheral rim (5h) enables, when the cone (7a) of the male Luer connector (7) presses against the elastic seal (5), to crush said peripheral rim (5h) between said cone (7a) and the ring (4). This results in a better load transfer and a better centering of the ring (4)/seal (5) assembly with respect to the chamber (3). The connection is performed in optimal fashion. Further, the system tightness is thus guaranteed.

In connected position, the free portion of the needle (6) is thus entirely contained within the inner channel of the cone (7a), thus allowing the transmission of fluid from connector (1) to connector (7). The motion of the ring (4) during this operation, is a homogenous uniform axial motion due to the permanent contact of the walls of the cross-sections of the ring (4) with the central compartment (3b) of the chamber (3) all along the motion, with a minimum friction. As shown in FIG. 6, in compressed position of the elastic seal (5), the portion of the ring (4) of small cross-section is in contact neither with the terminal compartment (3c) of the chamber (3), nor with the central compartment (3b) of the chamber (3). In practice, the volume of the central compartment (3b) of the chamber (3) is provided to be able to contain the volume of the seal (5) in compressed position.

As appears from the foregoing, the invention provides a medical connector (1) which is fully satisfactory in terms of use. The total tightness of the system obtained upstream of the terminal slit (5d) of the elastic seal (5) should in particular be noted. The connector (1) according to the invention further provides a maximum tightness of the connection with another male Luer connector (7), an increased decrease of risks of bacterial contamination of the terminal end of the chamber (3), and an optimal centering of the elastic seal (5) with respect to the terminal end of the chamber (3).

The invention claimed is:

1. A connector for a medical use comprising:
 a fitting secured to a chamber, the fitting comprising a needle provided at a center of the fitting, the needle extending in said chamber and emerging into a terminal end of the chamber, said terminal end of the chamber having a cross-section capable of receiving, by frictional engagement, a connector of male Luer type, the needle comprising at least one lateral through hole provided in a terminal portion of the needle;
 an elastic seal having a free end and a recess and having, across the thickness of the free end, a slit, the terminal portion of the needle being positioned within the recess of the elastic seal; and
 a ring encircling a portion of a terminal portion of the elastic seal in an area laterally opposite to the hole of the needle when the elastic seal is in a non-compressed position, wherein the terminal portion of the elastic seal comprises a terminal end having a deformable peripheral rim overlapping a free end of said ring.

2. The connector of claim 1, wherein the deformable peripheral rim is in contact with an internal wall of the chamber along an entire circumference of the internal wall.

3. The connector of claim 1, wherein the deformable peripheral rim is in contact with an internal edge of a free end of the chamber.

4. The connector of claim 3, wherein the deformable peripheral rim is positioned flush with the internal edge of the free end of the chamber.

5. The connector of claim 1, wherein the deformable peripheral rim is tangent to a free end of the chamber.

6. The connector of claim 1, wherein the deformable peripheral rim has a shape of a V directed towards an internal wall of the chamber.

7. The connector of claim 1, wherein the elastic seal has a substantially conical shape and comprises a base-forming portion, a median portion, and the terminal portion.

8. The connector of claim 7, wherein a wall of said median portion comprises a succession of beads defining, along the circumference of said seal, a wavy shape symmetrical with respect to an axial plane of said elastic seal.

9. The connector of claim 8, wherein the wavy shape corresponds to two sinusoid periods.

10. The connector of claim 7, wherein a wall of said median portion comprises, along the circumference of said seal, a succession of non-through cavities of elliptic shapes offset by one half-step every 90° around said circumference.

11. The connector of claim 1, wherein a base of the elastic seal is provided with a continuous peripheral groove directed upstream of the connector.

12. The connector of claim 1, wherein the deformable peripheral rim extends radially outward of the free end of the ring.

* * * * *